United States Patent
Weill et al.

(10) Patent No.: US 12,127,738 B2
(45) Date of Patent: Oct. 29, 2024

(54) TIP AND DEVICE FOR APPLYING AND SPREADING A LIQUID, GEL OR PASTE PRODUCT

(71) Applicant: PRIMEQUAL SA, Begnins (CH)

(72) Inventors: David Weill, Begnins (CH); Jérémy Charpilloz, Vessy (CH); Philippe Prost-Petit-Jean, Bonlieu (FR)

(73) Assignee: PRIMEQUAL SA, Begnins (CH)

( * ) Notice: Subject to any disclaimer, the term of this patent is extended or adjusted under 35 U.S.C. 154(b) by 731 days.

(21) Appl. No.: 17/042,825

(22) PCT Filed: Mar. 28, 2019

(86) PCT No.: PCT/IB2019/052560
§ 371 (c)(1),
(2) Date: Sep. 28, 2020

(87) PCT Pub. No.: WO2019/186465
PCT Pub. Date: Oct. 3, 2019

(65) Prior Publication Data
US 2021/0015473 A1  Jan. 21, 2021

(30) Foreign Application Priority Data
Mar. 29, 2018  (FR) .................................. 1852712

(51) Int. Cl.
*A61B 17/00* (2006.01)
*A61B 90/00* (2016.01)
*B05C 17/005* (2006.01)

(52) U.S. Cl.
CPC .. *A61B 17/00491* (2013.01); *B05C 17/00513* (2013.01); *B05C 17/00516* (2013.01);
(Continued)

(58) Field of Classification Search
CPC .... A61B 17/00491; A61B 2017/00473; A61B 2017/00495; A61B 2090/0807;
(Continued)

(56) References Cited

U.S. PATENT DOCUMENTS 4,430,075 A     2/1984   Urban
4,768,954 A *   9/1988   Dragan ................ A47B 67/005
                                                      433/90
(Continued)

FOREIGN PATENT DOCUMENTS

WO      2005107961     11/2005
WO      2008107813      9/2008
(Continued)

OTHER PUBLICATIONS

International Search Report in PCT/IB2019/052560 mailed Jul. 18, 2019.

*Primary Examiner* — Mohamed G Gabr
(74) *Attorney, Agent, or Firm* — Wissing Miller LLP

(57) ABSTRACT

The invention concerns an application tip for a device for applying and spreading a liquid, gel or paste product on a given surface configured to allow a volume of product to be transformed and spread over a surface according to a pre-determined calibration (C) comprising, internally, a flow control means, —internally, at least one buffer volume, means for controlled dispersion of the product, and a device for applying and spreading a liquid, gel or paste product on a given surface comprising means for storing the product and an application tip according to the invention.

12 Claims, 5 Drawing Sheets

Figure 3:
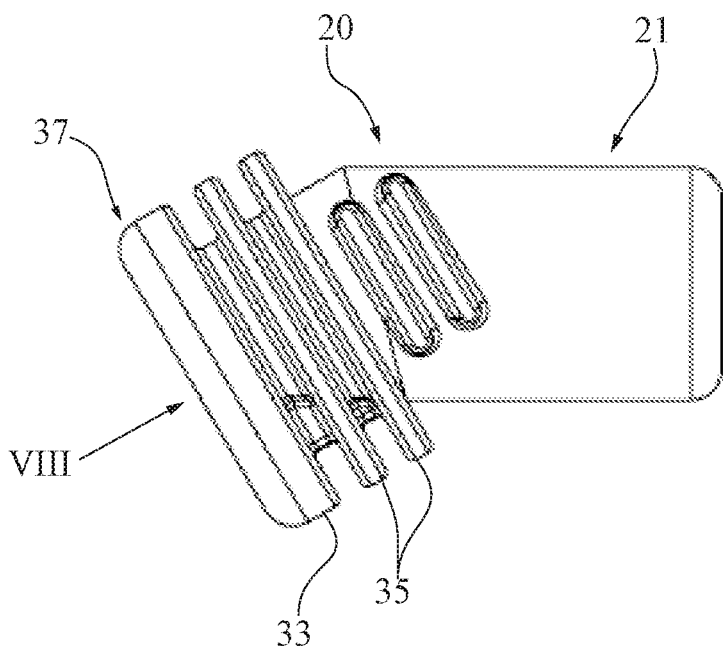

(52) U.S. Cl.
CPC ............... B05C 17/00593 (2013.01); *A61B 2017/00495* (2013.01); *A61B 2090/0807* (2016.02)

(58) Field of Classification Search
CPC ............. B05C 17/00; B05C 17/00516; B05C 17/00553; B05C 17/00593; B05C 17/00513
See application file for complete search history.

(56) References Cited

U.S. PATENT DOCUMENTS

| | | | |
|---|---|---|---|
| 5,944,698 | A | 8/1999 | Fischer |
| 6,637,967 | B2 * | 10/2003 | Bobo ............... A61B 17/00491 401/265 |
| 2003/0015557 | A1 | 1/2003 | D'Alessio |
| 2004/0122377 | A1 | 6/2004 | Fischer |
| 2005/0063768 | A1 | 3/2005 | Tani |
| 2005/0127119 | A1 * | 6/2005 | Keller ............... A61B 17/00491 222/556 |
| 2007/0014794 | A1 | 1/2007 | Carter |
| 2009/0108033 | A1 | 4/2009 | Quinn |
| 2013/0004230 | A1 | 1/2013 | Kirk, III |
| 2014/0016988 | A1 | 1/2014 | Bow |
| 2015/0266049 | A1 | 9/2015 | Ruiz, Sr. |
| 2016/0015373 | A1 | 1/2016 | Russo |

FOREIGN PATENT DOCUMENTS

| | | |
|---|---|---|
| WO | 2013144849 | 10/2013 |
| WO | 2017010953 | 1/2017 |

\* cited by examiner

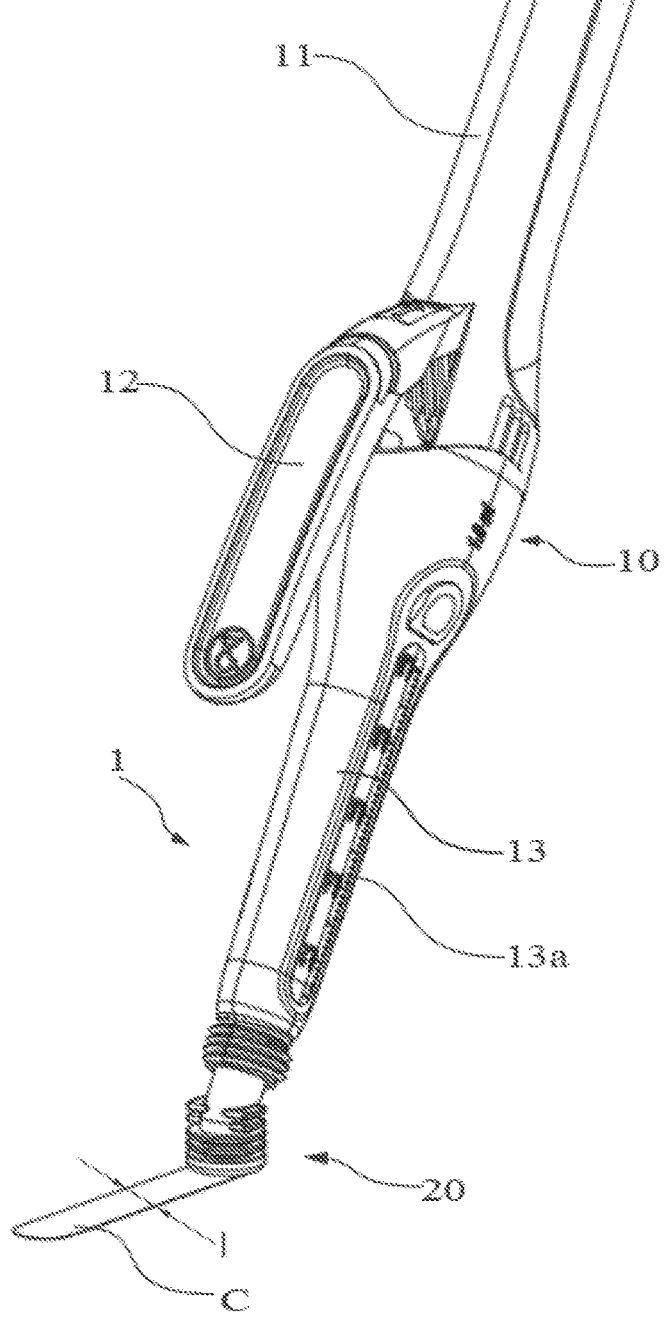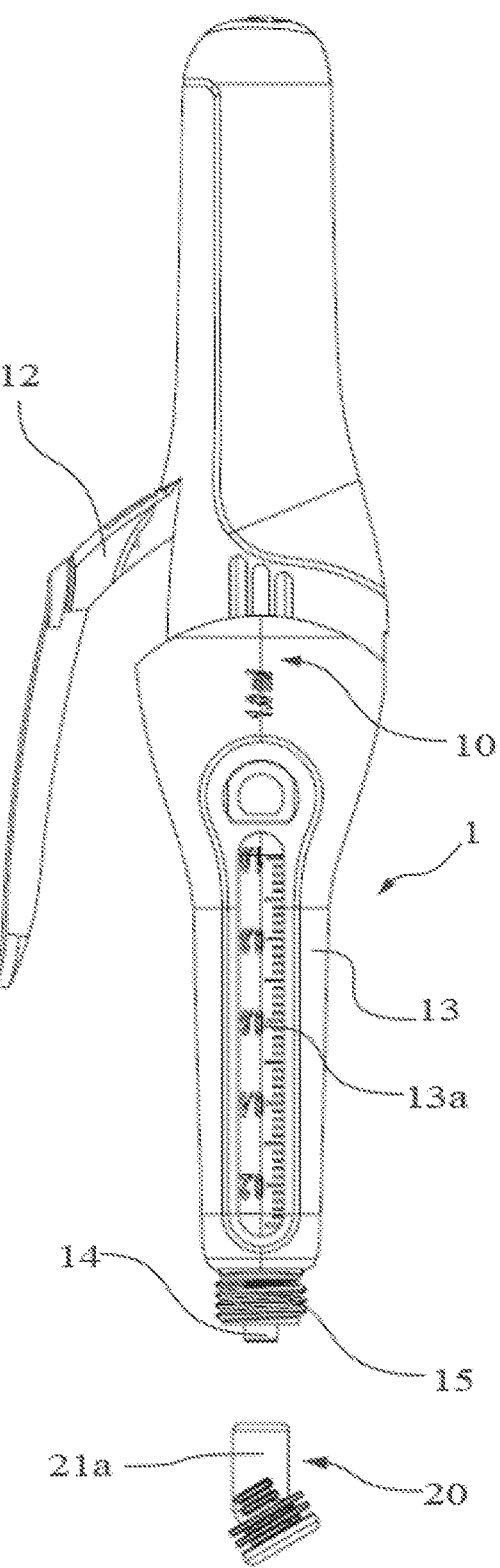

Fig.11
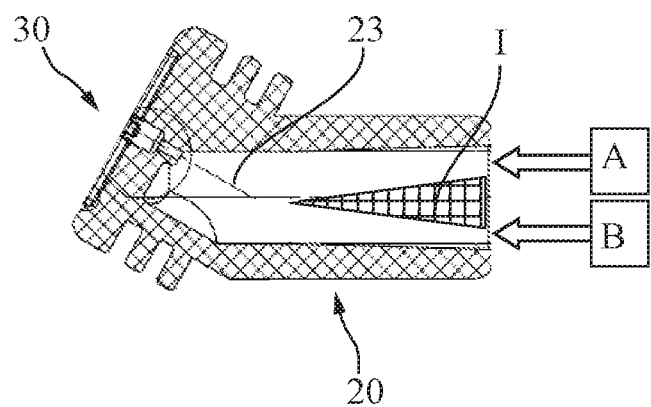
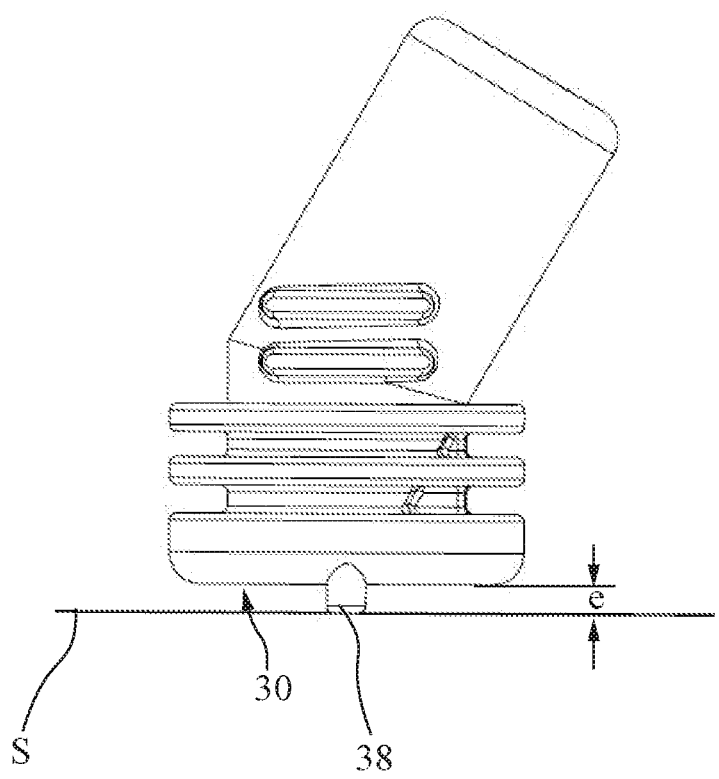
Fig.12

US 12,127,738 B2

TIP AND DEVICE FOR APPLYING AND SPREADING A LIQUID, GEL OR PASTE PRODUCT

This application is a 371 of PCT/IB2019/052560 filed on Mar. 28, 2019, published on Oct. 3, 2019 under publication number WO 2019/186465, which claims priority benefits from French Patent Application No. 18/52712, filed on Mar. 29, 2018, the disclosure of which is incorporated herein by reference.

The present invention relates to a tip for applying and spreading a liquid, gel or paste type product and a device comprising this tip.

It aims, in particular, to allow the application and spreading in a regular and smooth line of a product such as glue, industrial glue, medical glue, ointment, disinfectant, cream, lubricant, dye presented in the form of a liquid, paste, or gel.

It may be used, for example, for the application of so-called surgical glue in the field of medicine, in particular to close the edges of a wound or incision while avoiding the use of stitches or staples, which are unpleasant or even painful for the wearer to endure during the healing phase, wherein these stitches or staples then generally have to be removed after said healing phase.

In fact, the application of surgical-type glue requires great precision; the application must be carried out very regularly without jolts, leaving a controlled thickness and width of the bead of glue, preferably of the order of 4 mm on both sides of the wound, so as to ensure good closure of the edges of the wound and a good seal which is not liable to let in germs which could be harmful to good healing or cause infection.

To apply this type of glue, it is known, for example, from document WO 2017 010953 to use an application gun; however this type of gun is of complicated construction and only applies the glue point by point, which does not achieve a desired regular and controlled glue line.

Also known from document WO2013 144849 is a device for applying the glue at a certain distance from the user. In order to compensate for the extreme rigidity of the container, this device provides means for the forceful pressing on a tube to enable the glue to be delivered at a certain distance from the user. It does not provide for the application of the glue and even less for its spreading.

Document US 2007 0147947 A1 discloses a glue application system comprising a glue container and a kind of improved trowel. Such a device does not allow any control of the doses, nor any regularity of application of the glue.

From document US 2015 0266049 is also known a glue application device, in which the latter passes through a porous foam-type tip. Such a device does not allow precise spreading of the glue. In addition, this type of device clogs quickly since the glue passes through the foam without it being possible to remedy this because of the intrinsically sticky nature of the glue. For this reason, such devices are hardly usable in practice.

Finally, from document US 2016 0015373, a device is known which serves to allow the spreading of glue using a brush. The brush does not make it possible to obtain a regular surface, with, moreover, a risk of losing the bristles and having them mix with the product to be deposited which is a problem if it is a glue, which may eventually stick the bristles together.

The aim of the present invention is to remedy these drawbacks and to provide an application device for regularly and uniformly spreading a liquid, gel or paste type product.

It aims, in particular, to allow the smooth spreading along a regular line of a product, for example, of the adhesive type in the form of a liquid, paste or gel.

It aims, in particular, to allow spreading along a line of regular and homogeneous width and thickness.

This or these goals are achieved with the tip according to the invention and with the device for applying and spreading a liquid, gel or paste type product on a given surface according to the invention, comprising means for storing the product and an application tip according to the invention.

The present invention relates to an application tip for a device for applying and spreading a liquid, gel or paste type product on a given surface configured for allowing a volume of product to be transformed and spread on a surface according to a predetermined calibration (C) comprising
internally, a flow regulation means,
internally, at least one buffer volume,
means for the controlled dispersion of the product.

Preferably, the means for controlled dispersion of the product consist of at least one transverse groove on a surface at the end of the application tip.

Advantageously, the tip according to the invention comprises means for standardizing the dispersion of the product, wherein the means for standardizing the dispersion of the product preferably consist of dispersion grooves arranged in the form of a cross.

The present invention also relates to a device for applying and spreading a liquid, gel or paste type product on a given surface comprising means for storing the product, said device further comprising an application tip according to the present invention.

The tip and the device according to the invention are of simple design. In addition, they may be easily cleaned and sterilized, which is particularly advantageous for medical type applications.

According to the invention, the application tip comprises two parts, a part for "spreading" or "application" of the product and a part for "connection" or "connecting" to the ejection device.

In the present text, the expressions "spreading part" and "application part" refer to the same part; while the terms "connection part" and "connecting part" are used interchangeably.

Advantageously, the tip according to the invention comprises a connection part of cylindrical shape and a cylindrically-shaped application and spreading part of larger diameter than that of the connection part.

Preferably, the application tip according to the invention is designed in such a manner that the longitudinal axis L2 of the application and spreading part is inclined relative to the longitudinal axis L1 of the connection part. Preferably, the application tip according to the invention is designed in such a manner that the longitudinal axis L2 of the application and spreading part is inclined at an angle α (alpha) covering from 90 to 180°, preferably 135° relative to the longitudinal axis L1 of the connection part.

Advantageously, the tip according to the invention comprises means for spreading the product along a flat surface.

Advantageously, the tip according to the invention comprises gripping means.

According to the invention, the application tip comprises internally at least one buffer volume provided so as to maintain a predetermined 3D volume for the time necessary for the reduction of said volume of product in the tip as a result of spreading the product. This arrangement guarantees that there is no interruption in the flow of product during the entire operation, and therefore this makes it possible to guarantee the spreading along a regular line and without interruption, unlike the glue application devices, for example surgical, known until now. It is therefore possible to apply the latter in a continuous bead.

According to the invention, the application tip comprises internally at least one flow regulating means, wherein the flow regulating means may consist of a calibrated through-hole or a more elaborate device of the limiting valve type. Flow regulation is a physical means of regulating the thickness of the two-dimensional surface (2D surface) constituting the line or bead of glue. By moving the device at a regular speed, the product is released with a regular flow and the thickness and surface of the bonding line will be constant and controlled.

According to one embodiment, the buffer volume is disposed upstream of the means for regulating the flow rate.

According to another embodiment, the buffer volume is disposed downstream of the means for regulating the flow rate. According to a particular embodiment, the buffer volume is disposed at the outlet of the flow rate regulating means.

The tip according to the invention may comprise several buffer volumes located upstream of the flow rate regulating means and/or downstream of the flow rate regulating means. Advantageously, the tip according to the invention may comprise a buffer volume disposed upstream of the flow regulating means, a buffer volume disposed downstream of the flow regulating means, and a buffer volume disposed at the outlet of the flow regulating means.

According to the invention, the application tip comprises means for controlled dispersion of the product. In fact, since we want to transform a volume in three dimensions or 3D, (the drop of product) into a volume in two dimensions or 2D (the line or bead of product or glue according to a determined thickness), it is important to have means allowing the transport of the product (liquid, paste, gel) in another direction, namely in width (i.e. in the transverse direction with respect to the direction of application), wherein these means may be formed by at least one transverse groove arranged at the end of the application tip.

Advantageously, the tip according to the present invention comprises means for standardizing the dispersion of the product. In order to guarantee the uniformity of the dispersion regardless of the position of the device and/or of the application tip, the dispersion means is advantageously in the form of dispersion grooves arranged, for example, in the form of a cross or any other shape suitable for the product to be dispersed.

The tip according to the invention is advantageously made as a single part. It may thus be particularly compact. In addition, it has many parts having several functions. It may be produced by plastic injection and therefore at low cost and may be reused and/or cleaned and/or sterilized easily.

It is also compatible with existing product ejection devices on the market.

Figure 4:
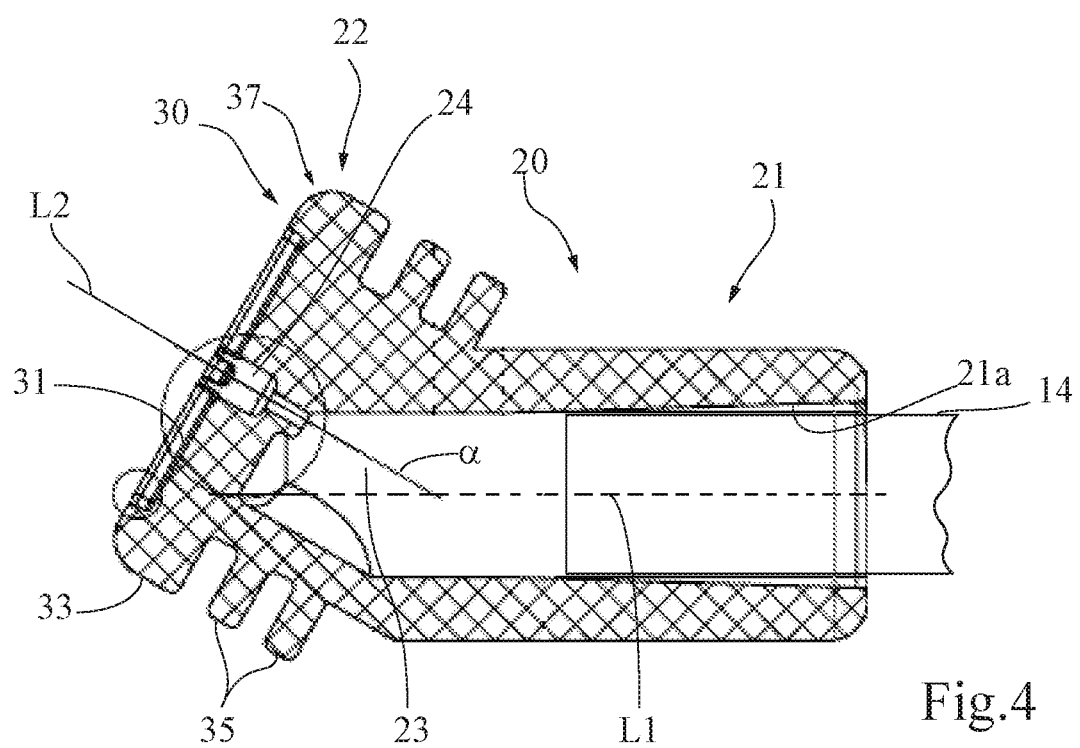
Figure 5:
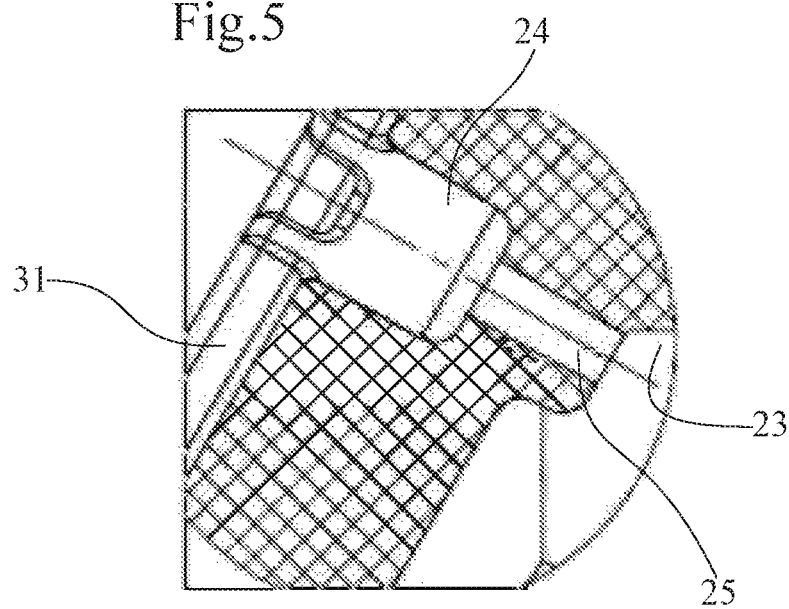
Figure 6:
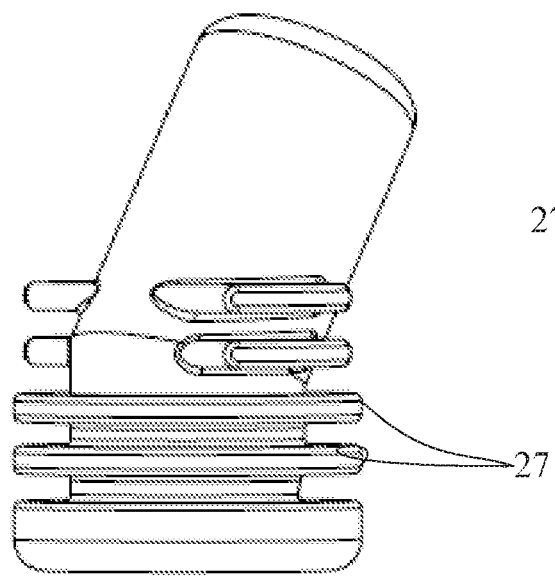
Figure 7:
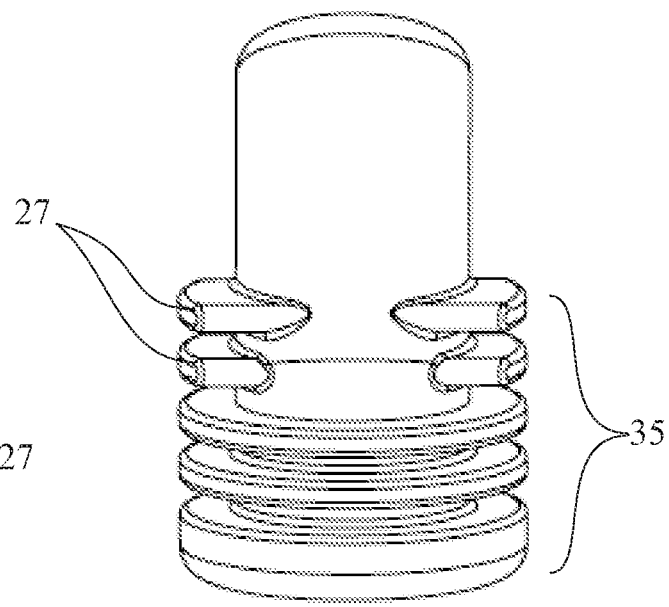
Figure 8:
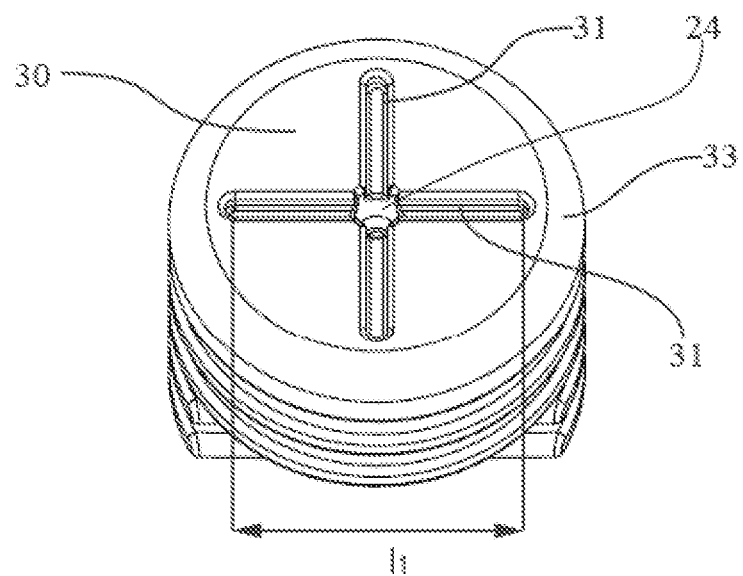
Figure 9:
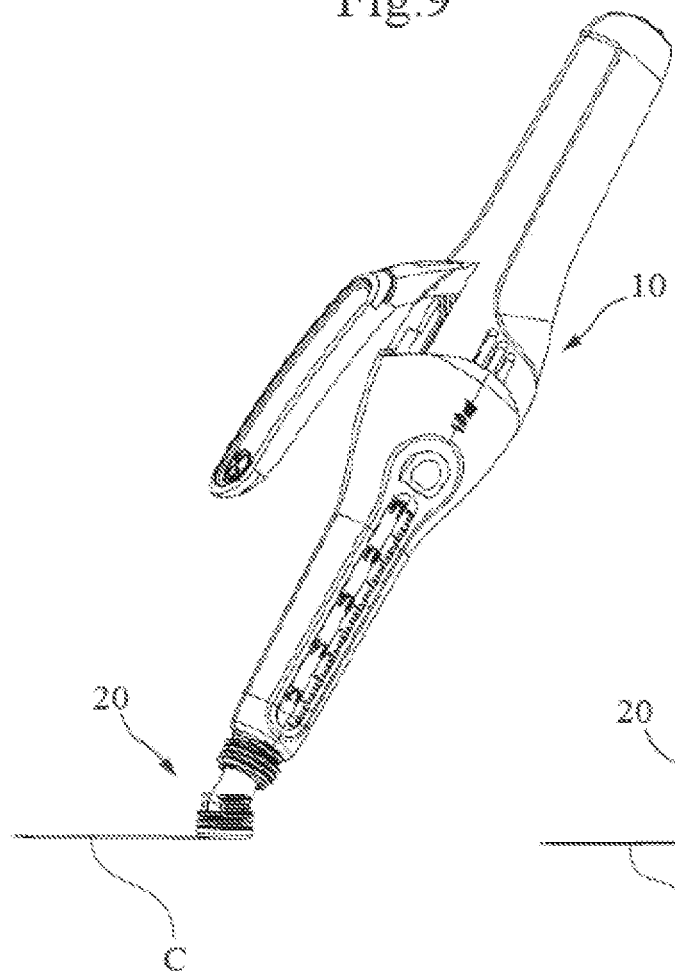
Figure 10:
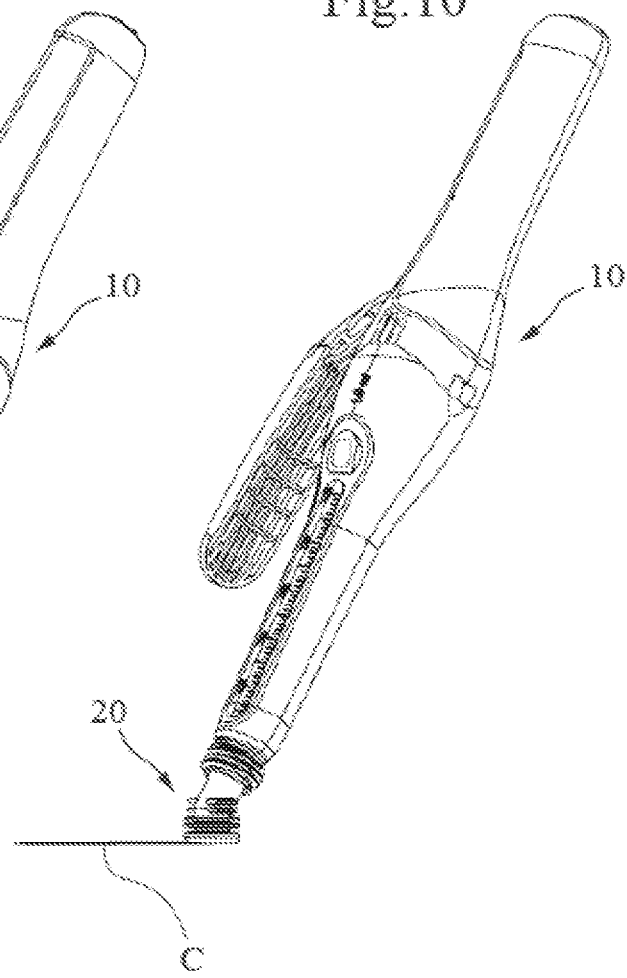

Other characteristics and advantages of the present invention may be demonstrated with the aid of the following description of at least one non-limiting example of execution with reference to the appended schematic drawings in which:

FIG. 1 is a front perspective view of the application and spreading device in use, FIG. 2 is a side view of the device of FIG. 1, with the application tip before fitting on the ejection device, FIG. 3 is, on an enlarged scale, a side view of the tip of FIG. 2, FIG. 4 is a longitudinal sectional view of the tip of FIG. 3, FIG. 5 is, on an enlarged scale, a detail view of FIG. 4, FIG. 6 is a side view of the tip in the application and spreading position, FIG. 7 is a front view of the tip of FIG. 6, FIG. 8 is a view of the tip according to arrow VIII of FIG. 3, FIGS. 9 and 10 show side views illustrating different ways of using the application device according to the invention, FIG. 11 is a view similar to FIG. 3 showing the mixture of two components in the tip, FIG. 12 is a view similar to FIG. 6 according to another embodiment.

In the following description, the elements of the device for applying and spreading a liquid, paste or gel type product according to the invention which are known per se to those skilled in the art will only be described in a simplified manner. In the following, we will denote by 3D volume a three-dimensional volume, for example a drop, and we will speak by contrast of a 2D surface, i.e. of a two-dimensional surface, even if it has a certain thickness but that may be considered as low to negligible compared to the rest of the surface and the volume. Similar or identical elements of the different embodiments will be designated by identical references.

As shown more particularly in FIGS. 1 and 2, the application and spreading device 1 of a product according to the invention comprises an ejection device 10 of a type known per se, and an application and spreading tip 20 to apply and spread the product in a continuous line or bead C and regular width I.

The ejection device shown comprises a rear body 11, intended to be held in the hand and having a suitable gripping shape, it also comprises a reservoir 13 for the product to be applied and spread and, in the case in question, means 14, 15 for connection to a removable application tip 20 respectively by screwing 15 or by a conically-shaped part 14. The reservoir 13 is provided with a graduated viewing window 13a. In this example, the rear body also comprises a ratchet lever 12 (not shown) serving to allow the ejection of the product. Such a device is already known and described, for example, in document WO 2008/107813. Of course any other type of ejection is possible depending on the type of product to be applied. For example, the system may be a piston system, syringe type, or, in the case of a very fluid product, the ratchet or piston device may be dispensed and the application may be carried out solely by means of gravity. Depending on the type of product to be applied and the field of use, and, in particular, in the medical field, it is advantageous for the ejection device to have elements, such as a ratchet system as described in document WO 2008/107813, allowing the release of a regular and precise dosage of the volume of product to be deposited and spread.

As shown in FIG. 4, the application tip 20 comprises a part 21 for connection to an ejection device and a part 22 for spreading the product delivered by the ejection device. The connection part 21, of generally cylindrical shape, is provided internally with a cylindrical recess 21a having a substantially conical shape that is complementary to that of the connection means 14 of the ejection device so as to be able to connect said application tip 20 to the connection means 14 by wedging.

In the example shown in FIG. 4, the conical wedging parts 21a comply with the Luer medical standard, while we may also consider Morse taper type connection systems or screw systems (using, for example, standard pitch screws, a specific screw thread, a Luer screw thread (Luer lock), or locking connection systems, for example of the bayonet or clip type. It should be noted that connection according to the Luer standard allows connection to all known medical devices of the syringe type or precision dosing system such as the ratchet type mentioned above.

The tip 20 comprises a spreading part 22 of generally cylindrical shape having a diameter greater than that of the connection part 21, the spreading part 22 being intended more particularly for the application and spreading of the product. The longitudinal axis L2 of the spreading part 22 is inclined at an angle α (alpha) ranging from 90 to 180°, preferably 135° in the example shown, with respect to the longitudinal axis L1 of the connection part 21. This arrangement makes it possible to provide good ergonomics of the assembly, as will be seen below. The free end of the spreading part 22 defines a spreading surface 30 which will be described in more detail later.

The spreading part 22 comprises, internally, a flow regulating means 25. With reference to the direction of flow of the product in the tip, the spreading part 22 comprises upstream of the flow rate regulating means 25, a first recess 23 delivering a determined volume. This first recess 23 is intended to serve as a buffer volume for the product to be applied and spread. It is, in fact, a matter of transforming a 3D volume, for example in the form of a drop, into a 2D volume, i.e. a "2D" spread surface, the thickness of said "surface" being considered negligible compared to the 3D volume to be spread. This buffer volume is provided so as to maintain a predetermined volume of product for the time required to reduce the volume of product in the tip as the product is spread. At least one other recess 24 or 31, located downstream of the flow rate regulating means 25, may also be provided; the recesses 24 and 31 are generally smaller in size. The recess 31 is provided in the thickness of the spreading surface 30, the recess 24 is provided upstream of the recess 31 in the part 22 of the tip, while the recess 24 is advantageously located at the outlet of the flow rate regulating means 25. These recesses are intended to also serve as buffer volumes and to be integrated separately or cumulatively depending on requirements and, in particular, on the type of product to be spread, its viscosity and the desired spreading width. The recess 24 has a substantially cylindrical shape; it is arranged along the axis L2 of the part 22 of the tip and opens out centrally into the spreading surface 30. According to FIG. 4 the recess 31 is formed by two slots substantially rectangular 31 formed in the spreading surface 30 and arranged at 90° relative to each other.

This arrangement ensures that there is no interruption of the flow of product during the entire application and spreading operation, therefore making it possible to ensure spreading along a regular line and without interruption, unlike the application devices of surgical glue known until now. It therefore becomes possible to apply the product regularly and smoothly in a continuous bead of the desired width and thickness. Of course, the recesses described may be chosen with different shapes and/or volumes depending on the product to be applied.

To ensure a determined thickness of the applied bead of product, provision may be made to add, for example, on the spreading surface 30 shapes, for example lugs 38 as shown in FIG. 12 making it possible to guarantee a distance at a determined interval between said surface 30 and the application surface in the manner of a spacer.

It should be noted that depending on the type of product used, for example if it is an adhesive or other type of product subject to polymerization, or with a high agglutination capacity, it may be important to provide a zone avoiding any clogging during the delivery of the product. The recess 23 may, in this case, be provided with a determined geometric shape, for example the large widening shown so as to prevent clumping and plugging.

As shown more particularly in FIG. 5, the application tip 20 also comprises a constriction 25 of cylindrical shape with a cross section between the recess 23 and the recess 24 where the cross section of constriction 25 is smaller than the cross sections of recesses 23 and 24. The purpose of this constriction 25, arranged upstream of the application part of the actual spreading surface 30, is to constitute a means of regulating the flow, in order to physically limit the quantity of product arriving on the spreading face as well as to physically regulate the thickness of the 2D surface. Thus, by moving the device 1 at regular speed over the surface to be covered, the product is released at a regular rate and the thickness of the surface is necessarily controlled and constant. Such a constriction may be replaced by any flow-limiting means, such as, for example, a limiting valve.

As indicated above, the spreading surface 30 comprises in the exemplary embodiment, two substantially rectangular slots 31 arranged in the form of a cross and communicating with the interior space 24 to receive and allow the spreading of the product. In addition to the buffer volume function described above, these slots 31 also fulfill two other functions. First of all, their length l1 determines the width 1 of the bead to be applied; these slots also serve as a guide for the flow of the product. Depending on the shape of the desired bead and the product to be applied, these slots 31 may have a different shape, be wider, longer and/or have a length different from the desired bead width C. Furthermore, the arrangement of said slots in the form of a cross makes it possible to reduce the influence of a potential rotation of the device in the user's hand during the application of the product, while ensuring dispersion of the product over a constant and regular surface. Of course an arrangement other than a cross may be provided depending on the product and type of application desired. It will also be possible to have a different number of slots 31. It should be noted that the outlet of the recess 24 which supplies the product is arranged in the center of the cross formed by the slots in order to guarantee an even distribution of the product.

Advantageously, the application tip comprises means for spreading the product along a flat surface 30. As shown in FIG. 8, the spreading surface 30 has a circular and generally flat shape, except for the grooves 31, which allows a face bearing on the surface to be treated to be generally flat, and therefore allow better contact, including under pressure on said surface when necessary. As shown in FIG. 3, said spreading surface 30 also has a rounded peripheral chamfer 37 which facilitates the sliding of the device over the surface to be treated and limits the blockages which may be inherent, for example, as a result of manual application. The chamfer is, of course, a function of the type of surface, its composition, its regularity. A large chamfer may, in particular, be advantageous in order to slide more easily on a soft or irregular surface, such as, for example, the skin.

The wedging mounting of the tip 20 in the application device 10 allows mounting in different orientations of the tip 20 on said device 10; this function is particularly interesting when the application must be carried out manually as in the example shown. In fact the different positioning possibilities make it possible to ensure good adaptation to the morphology of the hand and to the gestures of the user and thus make it possible to ensure a homogeneous result whoever the user, as illustrated in FIGS. 9 and 10.

FIG. 11 shows that the tip according to the invention may be used advantageously with two-component products (for example two-component glue). In this case the two components A and B are injected in a manner known per se by the mixing system and the mixing takes place beyond an injection cone I (which may be of variable shape and size), as close as possible to the zone 23 for transforming the 3D volume into 2D.

As shown in FIGS. 3, 6 and 7, the tip 20 comprises externally two series of circular peripheral fins 35 and two pairs of fins 27 arranged diametrically opposite. The series of circular peripheral fins 35 are arranged on the outside of the application part 22 of the tip 20 near the spreading surface 30. The diametrically opposed pairs of fins 27 are arranged on the outside of the connection part 21 of the tip 20 or on the outside of the tip 20 at the intersection of the connection part 21 and the application part 22. These fins 27, 35 perform several functions, first of all to facilitate the gripping of the tip 20, in fact this tip is not always integrated into the application device and it is therefore advantageous in this case to add elements improving the grip in the hand and making it possible to act with sufficient force to secure the tip in the device. These fins may also make it possible to exchange heat in the event of an endothermic or exothermic reaction of the product to be delivered, either due to friction or to a physical/chemical reaction.

As shown in particular in FIG. 1, the shape of the tip 20 and more specifically its angularity makes it possible to keep a good view of the surface of the bead C spread during the application of the product.

The use of the tip with an application device as described in document WO 2008/107813 is particularly advantageous since this device delivers controlled doses of product. Thus, in the example of surgical glue, it was possible to successfully transform 20 microliters of glue into a strip 4 cm long by 8 mm wide.

Of course, the present invention is not limited to the embodiments described and encompasses all similar or equivalent embodiments. Although described in connection with medical devices for applying surgical glue, it may be used for the continuous and regular application of any other type of product and in particular, glue, industrial glue, ointment, disinfectant, cream, lubricant, dyes, paint, make-up, alcoholic gel, anesthetic products, sealant, etc. without departing from the scope of the present invention.

The invention claimed is:

1. An application tip for a device for applying and spreading a liquid, gel or paste type product on a given surface and for allowing a volume of product to be transformed and spread on the surface according to a predetermined calibration comprising internally, a means for regulating the flow rate, wherein the means for regulating flow comprises a constriction with a constricted cross section;

internally, at least one first buffer volume provided between the constriction and the device, wherein the first buffer volume has a first cross section that is larger than the constricted cross section, at least one second buffer volume provided on an end of the constriction opposite from the first buffer volume; and means for controlled dispersion of the product provided on an end of the second buffer volume opposite from the constriction, wherein the means for controlling dispersion comprises a planar face configured to be in contact with the surface, and a recess in the planar face, said recess comprising a least one groove connected to the second buffer volume.

2. The tip according to claim 1, wherein at least one groove comprises transverse groove on the planar face.

3. The tip according to claim 1, wherein the means for controlled dispersion comprises means for standardizing the dispersion of the product.

4. The tip according to claim 3, wherein the at least one groove comprises two grooves, and wherein the means for standardizing the dispersion of the product consist of the grooves arranged in the form of a cross.

5. The tip according to claim 1, wherein the tip comprises a cylindrical shaped connection part and a cylindrical shaped application and spreading part of greater diameter than that of the connection part.

6. The tip according to claim 5, wherein a longitudinal axis L2 of the application and spreading part is inclined relative to a longitudinal axis L1 of the connection part.

7. The tip according to claim 6 wherein the longitudinal axis L2 of the application and spreading part is inclined at an angle α covering from 90 to 180° relative to the longitudinal axis L1 of the connection part.

8. The tip according to claim 7, wherein the angle α is about 135° relative to the longitudinal axis L1 of the connection part.

9. The tip according to claim 1, wherein the surface is a flat surface and wherein the planar face comprises means for spreading the product along the flat surface.

10. The tip according to claim 1, further comprising gripping means.

11. The tip according to claim 1, wherein the tip consists of a single part.

12. A device for applying and spreading a liquid, gel or paste type product on a given surface comprising means for storing the product, wherein the device further comprises the application tip according to claim 1.

* * * * *